United States Patent [19]

Girard et al.

[11] Patent Number: 5,728,711
[45] Date of Patent: Mar. 17, 1998

[54] TREATMENT OF *H. PYLORI* INFECTIONS

[75] Inventors: Arthur E. Girard, Jewett City; Thomas D. Gootz, Deep River, both of Conn.

[73] Assignee: Pfizer Inc., New York, N.Y.

[21] Appl. No.: 764,655

[22] Filed: Dec. 2, 1996

Related U.S. Application Data

[63] Continuation of Ser. No. 409,786, Mar. 24, 1995, abandoned, which is a continuation of Ser. No. 224,362, Apr. 7, 1994, abandoned.

[51] Int. Cl.$^6$ .................................................. A61K 31/435
[52] U.S. Cl. ........................ 514/300; 514/396; 514/926; 514/927
[58] Field of Search ................................. 514/300, 396, 514/926, 927

[56] References Cited

U.S. PATENT DOCUMENTS

| | | |
|---|---|---|
| 5,116,821 | 5/1992 | Randall et al. |
| 5,164,402 | 11/1992 | Brighty .................. 514/300 |
| 5,196,205 | 3/1993 | Borody . |
| 5,447,923 | 9/1995 | Catrenich et al. |
| 5,476,669 | 12/1995 | Borody . |
| 5,478,818 | 12/1995 | Niimura et al. |
| 5,618,564 | 4/1997 | Kimura et al. |

FOREIGN PATENT DOCUMENTS

| | | |
|---|---|---|
| 533281 | 3/1993 | European Pat. Off. |
| 9203135 | 3/1992 | WIPO . |
| 9321920 | 11/1993 | WIPO . |

OTHER PUBLICATIONS

B. Marshall, The Lancet, 1774–May 1983.
J.R. Warren, The Lancet, 1273 (1983).
Fedotin, Modern Medicine, 60, 61–70 (1992).
Czinn et al, Adv. Pediatr. Infect. Dis. 1990, 5, 221–37.
NIH Consensus Devt. Conf., 77–79, Feb. 7–9, 1994.
Canton et al., Rev. Esp. Enf. Digest, 78 (Suppl. I), 98(102), abstract #P–209 (1990);.
Peyre et al., Rev. Esp. Enf. Digest, 78 (Suppl. I), 107, abstract #P–232 (1990);.
Daskalopoulos et al., Rev. Esp. Enf. Digest, 78 (Suppl. I), 113, abstract #P–244 (1990);.
Molnar et. al., Irish J. Med. Science, 161 (Suppl. 10), 99, abstract #T44 (1992);.
Bayerdörffer et al., Deutsche Medizinische Wochenschrift 112, 1407–1411 (1987); abstract.
Hardy et al., J. Antimicrob. Chemother, 22, 631–636 (1988);.
Sachdeva et al., ICAAC, 107, abstract # 41 (1989);.
Labenz et al., Rev. Esp. Enf. Digest, 78 (Suppl. I) 104, abstract #P–224 (1990);.
Glupczynski et al. The Lancet: May 9, 1987, 1096 (1987);.
Mertens et al., Antimicrob. Agents Chemother, 33, 256–257 (1989);.
Forsmark et al., J. Infect. Dis., 162, 998 (1990);.
Vicenzi et al., Rev. Esp. Enf. Digest, 78 (Suppl. I), 114, abstract #P–248 (1990).
Westblom et al., J. Infect, Dis., 165, 974–975 (1992);.
Haas et al., Antimicrob. Agents Chemother, 34, 1637–1641 91990);.
Caekenberghe et al., Antimicrobial Agents and Chemotherapy, 31, 1429–1430 (1987);.
Nakao et al., Eur. J. Clin. Microbiol. Infect. Dis., 14, 391–399 (1995);.
Colin–Jones, Lancet, 1467 (1987);.
NIH Consensus Development Conference on *Helicobacter pylori* in Peptic Ulcer Disease, Feb. 7–9 (1994);.
Carley et al., J. Antimicrobial Chemotherapy, 24, 266–268 (1989);.
Glupczynski et al., Eur. J. Epidemiol., 4, 154–157 (1988);.
McNulty et al., Eur. J. Clin. Microbiol Infect. Dis., 7,566—569 (1988);.
Marshall, Gastroenterology Clinics of North America, 22, 183–198 (1993);.
Simor et al., Antimicrobial Agents and Chemotherapy, 33, 108–109 (1989).

*Primary Examiner*—Rebecca Cook
*Attorney, Agent, or Firm*—Peter C. Richardson; Paul H. Ginsburg; Gezina Holtrust

[57] ABSTRACT

An infection with Helicobacter may successfully be treated with a compound of the formula

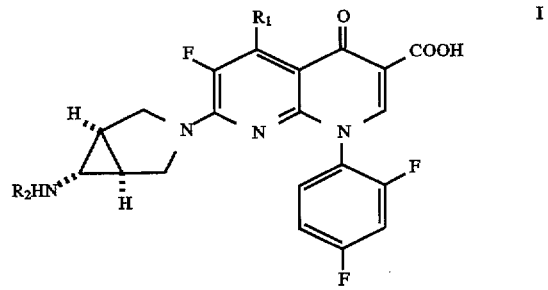

wherein $R_1$ is hydrogen or methyl and $R_2$ is hydrogen or L-alanine-L-alanyl, and the pharmaceutically acceptable acid additive salts thereof. These compounds are useful in the treatment of gastric and duodenal ulcers.

2 Claims, No Drawings

TREATMENT OF *H. PYLORI* INFECTIONS

This is a continuation, of application Ser. No. 409,786, filed on Mar. 24, 1995 which is a continuation of Ser. No. 08/224,362, Apr. 7, 1994 abandoned.

BACKGROUND OF THE INVENTION

This invention relates to a novel treatment of a Helicobacter infection with known naphthyridine carboxylic acid antibacterial compounds and a novel treatment of gastric and duodenal ulcers with such known compounds.

*H. pylori*, a pathogenic bacterium discovered in 1982, has been established as the cause of gastric and duodenal ulcers in humans. In clinical trials, eradication of the organism has been shown to result in healing of the ulcer and a low incidence of relapse. Although numerous individual antibacterial agents inhibit the growth of Helicobacter organisms in vitro, these agents usually fail in in vivo human and animal trials, when administered as single agents.

Infections in animals are caused by related organisms. For example, *H. mustelae* is pathogenic in ferrets, and *H. felis* in cats.

The compounds of use in this invention are disclosed in U.S. Pat. No. 5,164,402.

SUMMARY OF THE INVENTION

This invention relates to a method for the treatment of a Helicobacter pylori infection which comprises administering to a subject in need of such treatment an effective amount of a compound of the formula

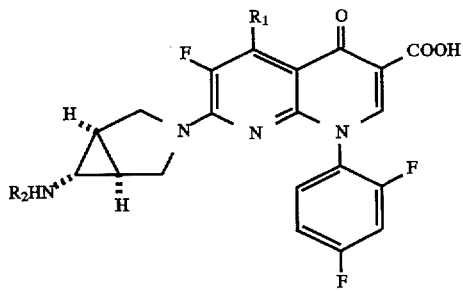

wherein $R_1$ is hydrogen or methyl and $R_2$ is hydrogen or L-alanine-L-alanyl, and the pharmaceutically acceptable acid addition salts thereof (the active compound).

In a specific embodiment of the invention said active compound is 7-([1α,5α, 6α]-6-amino-3-azabicyclo[3.1.0] hex-3-yl)-1-(2,4-difluorophenyl)-6-fluoro-1,4-dihydro-4-oxo-1,8-naphthyridine-3-carboxylic acid methanesulfonate.

The invention also relates to a method for the treatment of gastric and duodenal ulcers by administering to a subject in need of such treatment an effective amount of the active compound. In a specific embodiment, the compound used is 7-([1α, 5α, 6α]-6-amino -3-azabicyclo[3.1.0]hex-3-yl)-1-(2,4-difluorophenyl)-6-fluoro-1,4-dihydro-4-oxo-1,8-naphthyridine-3-carboxylic acid methanesulfonate.

DETAILED DESCRIPTION OF THE INVENTION

The active compounds and their preparation are disclosed in U.S. Pat. No. 5, 164,402.

As disclosed in U.S. Pat. No. 5,164,4.02, the compounds of formula I form pharmaceutically acceptable acid addition salts. All such salts are within the scope of this invention and can be prepared as described in U.S. Pat. No. 5,164,402. Examples of suitable acids are acetic, lactic, succinic, maleic, tartaric, citric, gluconic, ascorbic, benzoic, methanesulfonic, p-toluenesulfonic, cinnamic, fumaric, phosphonic, hydrochloric, hydrobromic, hydroiodic, sulfamic, and sulfonic acid.

According to the invention, the active compound may be used in combination with a second antimicrobial agent, such as nitroimidazole antibiotics, e.g. tinidazole and metronidazole; tetracyclines, e.g. tetracycline, doxycycline and minocycline; penicillins, e.g. amoxicillin, ampicillin and mezlocillin; cephalosporins, e.g. cefaclor, cefadroxil, cephadrine, cefuroxime, cefuroxime axetil, cephalexin, cefpodoxime proxetil, cefiazidime and ceftriaxone; carbapenems, e.g. imipenem and meropenem; aminoglycosides, e.g. paromomycin; macrolide antibiotics, e.g. erythromycin, clarithromycin and azithromycin; lincosamide antibiotics, e.g. clindamycin; rifamycins, e.g. rifampicin; and nitrofurantoin. Also included within the invention are combinations of the active compound with a pharmaceutical compound used in the treatment of acid-related disorders such as acid pump inhibitors, e.g. omeprazole and lansoprazole, or $H_2$ antagonists, e.g. ranitidine, cimetidine, and famotidine.

A preferred combination according to the invention is 7-([1α,5α, 6α]-6-amino-3-azabicyclo[3.1.0]hex-3-yl)-1-(2,4-difluorophenyl)-6-fluoro-1,4-dihydro-4-oxo-1,8-naphthyridine -3-carboxylic acid methanesulfonate and amoxicillin.

A second combination according to the invention is 7-([1α, 5α, 6α]-6-amino-3-azabicyclo[3.1.0]hex-3-yl)-1-(2,4-difluorophenyl)-6-fluoro-1,4-dihydro-4-oxo-1,8-naphthyridine-3-carboxylic acid methanesulfonate and tetracyclin.

A third preferred combination according to the invention is 7-[1α, 5α,6α]-6-amino-3-azabicyclo[3.1.0]hex-3-yl)-1-(2,4-difluorophenyl)-6-fluoro-1,4-4-oxo1,8naphthyridine-3-carboxylic acid methanesulfonate and omeprazole.

The active compounds are useful in the treatment of *H. pylori* in humans, and related Helicobacter infections in animals. They are also useful in the treatment of gastric and duodenal ulcers. As used herein, "treatment" is meant to include the eradication of the Helicobacter microorganism and the alleviation of the gastric and duodenal ulcers.

The active compounds of the invention may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules; either alone or in admixture with excipients, or in the form of elixirs or suspensions containing flavoring or coloring agents. In the case of animals, they are advantageously contained in an animal feed or drinking water in a concentration of 5–5000 ppm, preferably 25–500 ppm.

The active compounds wherein $R_2$ is L-alanine-L-alanyl can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1–50 mg/kg/day, advantageously 1–5 mg/kg/day given in a single daily dose or up to 3 divided doses.

The compounds of the invention can be administered to humans by either the oral or parenteral routes, and may be administered orally at dosage levels of about 0.1 to 50 mg/kg/day, advantageously 1–5mg/kg/day given in a single dose or up to 3 divided doses. For intramuscular or intravenous administration, dosage levels are about 0.1–50 mg/kg/day, advantageously 1–5 mg/kg/day. While intramuscular administration may be a single dose or up to 3 divided doses, intravenous administration can include a continuous drip. Variations will necessarily occur depending on the weight and condition of the subject being treated and the particular routes of administration chosen as will be known to those skilled in the art.

The activity of the active compounds in vitro may be shown by the following procedure.

Agar Dilution of Antimicrobial 6 mg. of the compound to be evaluated is solubilized in 0.6 ml 100% dimethylsulfoxide (DMSO) and then brought up to 6 ml with sterile brucella broth and the solubility is noted. The final concentration of DMSO is 10% of the total volume. Serial 2-fold dilutions (3 ml compound+3 ml brucella broth) are then made in sterile brucella broth. A 2 ml aliquot of each broth dilution within the series is placed in separate sterile petri dishes, to which 18 ml of melted and cooled (approx. 50° C.) brucella agar supplemented with 7% horse blood is added. This yields a final 1:10 dilution of compound in agar, and a final concentration of DMSO of 1%. For example, if the highest concentration (1st broth dilution) contains 1000 ug/ml, and is diluted 1:10 in agar, the final concentration of drug in agar is 100 ug/ml. Agar plates can be prepared one day prior to inoculating, and refrigerated overnight.

Inocula Preparation

*Helicobacter pylori* cultures are maintained on trypticase soy-5% sheep blood agar plates, and are transferred every 48 hours. *Helicobacter mustelae* cultures are maintained on the same agar, and are transferred every 48–60 hours, depending upon the extent of the growth of the previous transfer. Plates are incubated at 37° C. in GasPak jars with water-activated (10 ml) CampyPak Plus (BBL Microbio. Systems) envelopes with palladium catalyst.

*Helicobacter* cultures can be grown in brucella broth supplemented with 10% fetal calf serum in 10 ml volumes in deep petri dishes. The plates are incubated for 18–20 hours at 37° C. in GasPak jars with water-activated (10 ml) CampyPak Plus envelopes with palladium catalyst on a shaker at 50 rpm.

Overnight cultures (approx. $10^8$ CFU/ml) are diluted 10-fold in brucella broth (no FCS) in screw-capped tubes for use as the standard inoculum. The wells of a Steere replicator are filled with 0.8 ml of the diluted organism, and approximately $2 \times 10^4$ cells in 0.002 ml are placed on the agar surface. Inoculated plates are placed in a GasPak jar to which water-activated (10 ml) Campy Pak Plus envelopes with palladium catalyst have been added, and incubated at 37° C. for 48 hours.

Interpretation of Results

Following incubation, all test plates are compared to a compound-free growth control plate. The MIC is the concentration which inhibits growth compared to the control plate. A thin film of growth might be visible at higher concentrations but this is discounted, and not considered the true MIC. Control organisms are also inoculated on each plate, and these are diluted 1000-fold for use as inocula. The control organisms include *Campylobacter jejuni* (#668), and the screening cultures of *E.coli* (#51A266 and #51A470), *Enterobacter aerogenes* (#67A040), *E. cloacae* (#678009), *Providencia stuartii* (#77A013) and *P. rettgeri* (#77C025). Plates and/or inocula transfers should not be out of the microaerophilic environment longer than 2 hours. It is also recommended that all manipulations involving *Helicobacter* cultures be performed in a laminar flow hood to decrease the chance of contaminating the cultures with mold.

The mouse model of Lee et al., Gastroenterology, 99,1315–23(1990) is used to predict the in vivo activity of a compound against *H. pylori* in humans.

*Helicobacter felis* is grown in brucella broth with 10% fetal bovine serum. A frozen culture is quickly thawed; the culture is checked for motility and 0.5 cc. of the thawed frozen culture is inoculated into a deep tissue culture dish containing 9.5 cc. of the brucella/serum mix. The dishes are put into a Campy Pak jar [BBL] to insure a microaerophilic atmosphere. The jar is put on a rotary shaker at 60 RPM in a 37° C. incubator. After 18 hours there should be visible turbidity. The culture is checked for purity and motility under a (phase) microscope and then pooled into a flask. Swiss-Webster female mice (18–20 g) are fasted for 18 hours before infection. The mice are infected three times on alternate days during a single week. Dosing begins two weeks after the last dose of organism. Treatments are given once per day for fourteen consecutive days. Sacrifice is about three weeks after completion of therapy. For each mouse, the stomach is excised and opened along the greater curvature. A plug (a 3 min. tissue section) is taken from the antrum region of the stomach. The plug surface is washed, minced, and dropped into a tube with 100 microliters of urease reagent. The urease reagent is the reagent of Hazell et. al., Am. J. Gastroenterology, 82, 292–296 (1982). The urease reagent (pH 6.3–6.5) contains urea and phenol red. If Helicobacter is present, urease will break down urea producing a change of pH. Purple (alkaline) is positive for Helicobacter; red/yellow (no change) is negative. Any color change is recorded after 18 hours. There are usually twenty mice per treatment group; the percent positive for each group is recorded.

There are several methods used clinically to determine whether *Helicobacter pylori* is present in a human subject. These are employed for initial diagnosis of infection prior to treatment, as well as for determining the success of treatment in eradicating the organism from the patient.

The urea breath test involves ingestion of radiolabelled urea. *H. pylori* produces a urease enzyme which degrades urea; mammalian gastric cells do not contain this enzyme. Exhalation of labeled carbon dioxide (analyzed by mass spectrometry or radioactivity, depending on the isotope employed) therefore indicates that *H. pylori* is present.

Serology can also be used to assess infection with *H. pylori*. Detection of serum antibodies to *H. pylori*, such as IgG and IgA, is carried out using enzyme-linked immunosorbent assay (EUSA). Numerous different *H. pylori* proteins can be employed as antigens.

Endoscopy of the patient provides samples of tissue which can be cultured in a microaerophilic environment to diagnose *H. pylori* infection. Alternatively, the sample can be examined histologically by employing one of a number of stains such as Giemsa or hematoxylin-eosin. A urea test, which again takes advantage of the production of urease by *H. pylori*, can also be applied. This test relies on the formation of ammonia from the urea hydrolysis, which results in an observable change in pH.

We claim:

1. A method for the treatment of a *Helicobacter pylori* infection which comprises orally administering to a subject in need of said treatment an effective amount of 7-([1α, 5α, 6α]-6-amino-3 azabicyclo[3.1.0]hex-3-yl)-1-(2,4-difluorophenyl)-6-fluoro-1,4-dihydro-4-oxo-1,8-naphthyridine-3- carboxylicacid methanesulfonate at dosage levels of 1 to 5 mg/kg/day, in combination with an effective amount of metronidazole.

2. A method for the treatment of gastric or duodenal ulcers which comprises orally administering to a subject in need of said treatment an effective amount of 7-([1α, 5α, 6α]-6-amino-3-azabicyclo[3.1.0]hex-3-yl)-1-(2,4-difluorophenyl)-6-fluoro-1,4dihydro-4-oxo-1,8-naphthyridine-3-carboxylicacid methanesulfonate at dosage levels of 1 to 5 mg/kg/day, in combination with an effective amount of metronidazole.

* * * * *